(12) United States Patent
Fukushima et al.

(10) Patent No.: US 7,241,624 B2
(45) Date of Patent: Jul. 10, 2007

(54) DENDRIMER-BASED DNA EXTRACTION METHODS AND BIOCHIPS

(75) Inventors: Kazuhisa Fukushima, Musashino (JP); Saya Satou, Musashino (JP); Tadashi Matsunaga, 4-20-5 Hon-Cho, Koganei-shi Tokyo (JP); Haruko Takeyama, Koganei (JP)

(73) Assignees: Yokogawa Electric Corporation, Tokyo (JP); Tadashi Matsunaga, Tokyo (JP)

( * ) Notice: Subject to any disclaimer, the term of this patent is extended or adjusted under 35 U.S.C. 154(b) by 163 days.

(21) Appl. No.: 10/928,183

(22) Filed: Aug. 30, 2004

(65) Prior Publication Data

US 2005/0130191 A1    Jun. 16, 2005

(30) Foreign Application Priority Data

Dec. 16, 2003   (JP) ............................. 2003-417848

(51) Int. Cl.
- G01N 33/00 (2006.01)
- C12Q 1/68 (2006.01)
- C12M 3/00 (2006.01)
- C07H 21/04 (2006.01)

(52) U.S. Cl. .................. 436/94; 435/6; 435/287.2; 533/23.1; 533/24.3

(58) Field of Classification Search ............ 435/6, 435/287.2; 436/94; 536/23.1
See application file for complete search history.

(56) References Cited

U.S. PATENT DOCUMENTS 5,824,478 A * 10/1998 Muller ............................ 435/6

2004/0171097 A1 * 9/2004 Schneider-Mergener et al. 435/23
2005/0260600 A1 * 11/2005 Matsunaga et al. ............. 435/6

FOREIGN PATENT DOCUMENTS

| JP | 8-176212 | 7/1996 |
|---|---|---|
| JP | 11-313670 | 11/1999 |

OTHER PUBLICATIONS

Page 67-69 of "DNA Chips and It's Applications", Jul. 31, 2000 (Partial translation).
R. Benters et al., "Dendrimer-Activated Solid Supports for Nucleic Acid and Protein Microarrays" CHEMBIOCHEM, 2001 vol. 2, pp. 686-694.
Chinese Office Action dated Jul. 7, 2006, issued in corresponding Chinese Application No. 2004100984238.

* cited by examiner

Primary Examiner—Bradley L. Sisson
(74) Attorney, Agent, or Firm—Westerman, Hattori, Daniels & Adrian, LLP.

(57) ABSTRACT

The present invention provides a dendrimer-based biochip, wherein a flow channel through which a solution containing biopolymer molecules is flowed is formed in the substrate of the biochip, a plurality of dendrimer molecules one end of each of which is bound to the walls of the flow channel are formed thereon, and probe biopolymer or antibody molecules are bound to the tips of the dendrimer molecules so that, if the probe biopolymer molecules are bound, then target biopolymer molecules can be captured by means of a complementary combination and, if the antibody molecules are bound, then protein can be extracted by means of antigen-antibody reaction, whereby biopolymers can be retrieved in a highly efficient manner.

2 Claims, 2 Drawing Sheets

DENDRIMER-BASED DNA EXTRACTION METHODS AND BIOCHIPS

BACKGROUND OF THE INVENTION

1. Field of the Invention

The present invention relates to a method and a biochip for efficiently retrieving (or alternatively referred to as "extracting") biopolymers such as DNA, RNA and protein from affected cells, for example, by producing dendrimer molecules in the flow channel of the biochip's preprocessing area.

2. Description of the Prior Art

The prior art is explained hereinafter by taking DNA as an example of a biopolymer. The target DNA used for DNA chips is retrieved by means of preprocessing.

Methods of retrieving DNA from affected cells or the like dissolved in blood serum, lymphocyte-clastic solution or lysis buffer solution, for example, are roughly classified into two types: the centrifugal separation method and the magnetic bead method.

Since the centrifugal separation method involves the use of large-scale apparatus, the magnetic bead method is expected to become mainstream in the future where downsizing is required.

Accordingly, the magnetic bead method is discussed hereinafter. (See non-patent document 1, for example, for details on examples of applications of magnetic beads. It should be noted that the material on which this method is based, is referred to not only as magnetic bead, but also as magnetic particle or magnetic body. See patent document 1, for example, for details on examples of applications of the method in which the material is referred to as magnetic particles. Likewise, see patent document 2, for example, for details on examples of applications of the method in which the material is referred to as magnetic body.)

The magnetic bead method is a DNA retrieval method in which molecules of probe DNA or probe antibody are bound to the surfaces of magnetic beads at a specific density, and DNA in a solution is retrieved by means of a complementary combination of target DNA molecules in the solution and probe molecules. Then the magnetic beads are collected and cleaned using a magnet and the DNA is dissociated from the surfaces of the magnetic beads using a solution and is thus retrieved.

Non-Patent Document 1

Haruko Takeyama and Hideki Nakayaka, Chapter 7 "DNA Chips Using Magnetic Beads" in "DNA Chips and It's Application" published by CMC Publishing Co., Ltd. in July 2000 under the editorship of Tadashi Matsunaga Patent Document 1

Japanese Laid-open Patent Application 1996-176212

Patent Document 2

Japanese Laid-open Patent Application 1999-313670

However, while apparatus using the magnetic bead method is smaller and more convenient than those using the centrifugal separation method, the magnetic bead method has difficulty in binding probes to the surfaces of magnetic beads at an appropriate density. Thus, the efficiency of DNA retrieval is currently at issue. In addition, it is cumbersome to collect magnetic beads with a magnet and then retrieve DNA from the surfaces of the beads. Therefore, an even simpler method of DNA retrieval is required in order to transform the preprocessing area into a chip in the future.

SUMMARY OF THE INVENTION

The present invention is intended to solve the aforementioned problems. One object of the present invention therefore, is to provide a method for retrieving biopolymers in a highly efficient manner by taking advantage of the dendrimers' ability to achieve highly efficient densities because of their freely controllable structural density, as well as a biochip using dendrimers.

Another object of the present invention is to provide a dendrimer-based biochip that has no mechanical moving parts and whose preprocessing area can be easily miniaturized.

DESCRIPTION OF THE PREFERRED EMBODIMENTS

In the present invention, a dendrimer structure is formed in a flow channel through which a DNA solution flows, by taking advantage of the ability of dendrimers to achieve highly efficient densities because of their freely controllable structural density. Then, probe polymer molecules complementary with target biopolymer molecules are bound to the tips of dendrimers so that these biopolymer molecules are retrieved in a highly efficient manner. In addition, the conventional method using magnetic beads requires mechanical moving parts since magnetic beads are first collected and then DNA is retrieved from their surfaces. The present invention eliminates the need for such mechanical moving parts, thereby enabling the preprocessing area to be easily miniaturized.

Figure 1:
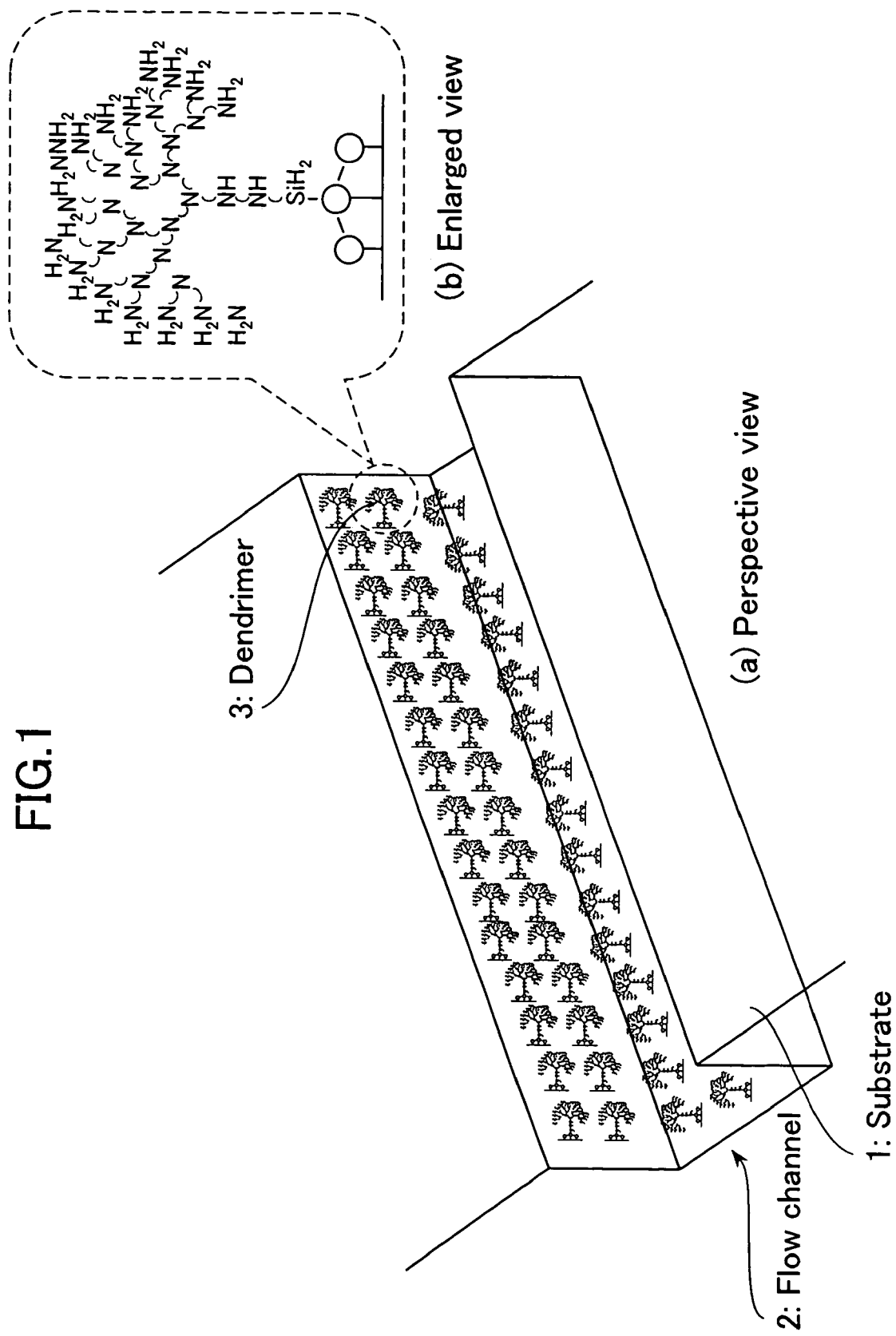
FIG. 1 is a schematic view illustrating one embodiment of a flow channel formed in the preprocessing area of a dendrimer-based biochip in accordance with the present invention.

The present invention will hereinafter be described in detail with reference to the accompanying drawings. FIG. 1 is a schematic view illustrating one embodiment of a flow channel formed in the preprocessing area of a dendrimer-based biochip in accordance with the present invention, wherein FIG. 1(a) is a perspective projection (partially perspective view) of the surfaces of a substrate, and FIG. 1(b) is an enlarged view of a dendrimer molecule.

In FIG. 1, numeral 1 denotes the substrate of a biochip and numeral 2 denotes a flow channel through which a DNA solution flows, and numeral 3 denotes a dendrimer molecule bound to flow channel 2.

Substrate 1 is made of such materials as glass or plastics and U-shaped flow channel 2 is formed in substrate 1. A plurality of molecules of dendrimer 3 is formed on the walls of flow channel 2.

Dendrimer 3 is, for example, a multibranched polyamide amine dendrimer and is produced by providing aminosilane treatment on the surfaces of flow channel 2 and overlaying a film of amidoamine, which is produced by the reaction of methyl acrylate with ethylenediamine, upon the aminosilane-treated area as a dendron unit.

Probe DNA is bound to the tip (surface) of dendrimer 3 which goes into a complementary combination with target DNA.

When a solution containing target DNA is poured into the biochip structured as described above and is made to flow through flow channel 2, the target DNA combines with the probe DNA in a complementary manner. Consequently, the target DNA is captured in a highly efficient manner.

It should be noted that the density of probe DNA molecules bound to the tips of dendrimer molecules has the optimum value, depending on the type of target (DNA, mRNA or protein). This optimum value can be obtained by changing the number of dendrimer layers (generations). Under normal conditions, second or higher generation dendrimers are used.

It is to be understood that the present invention is not restricted to the foregoing embodiments; rather, many other alterations and modifications thereof may be made without departing from the spirit and essential characteristics thereof. It is therefore intended that such alterations and modifications be covered by the appended claims.

Figure 2:
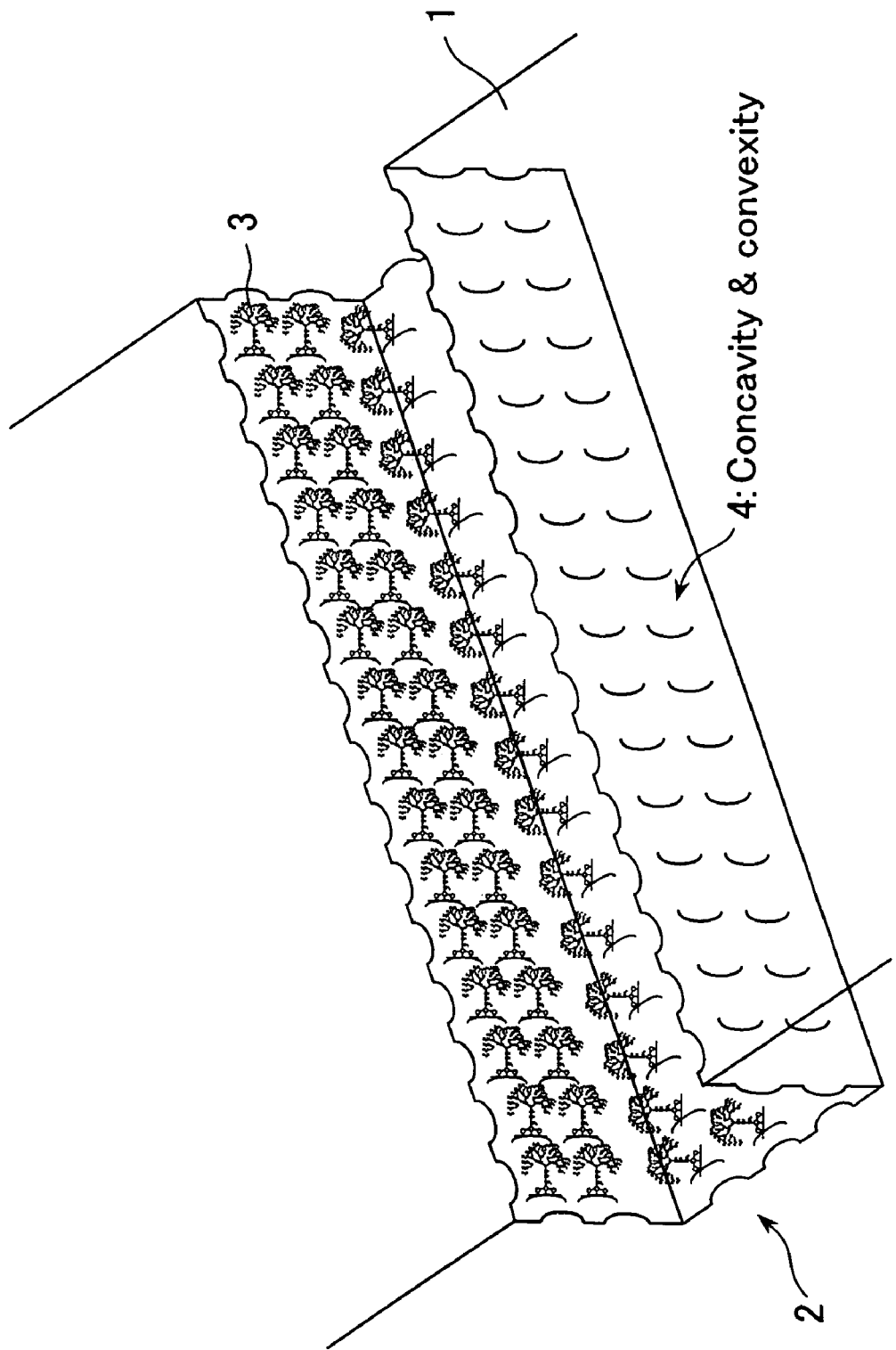
FIG. 2 is a schematic view illustrating another embodiment of the flow channel.

For example, a plurality of concavities and convexities 4 may be formed on the walls of flow channel 2 so that turbulence takes place when a solution containing target DNA flows through flow channel 2, as illustrated in FIG. 2. This turbulence further increases the efficiency of the complementary combination between target DNA and probe DNA.

In the foregoing embodiments, an example has been shown wherein DNA segments are bound to the surfaces of dendrimer molecules and target and probe molecules are combined by means of hybridization. Alternatively, molecules of a biopolymer probe other than DNA may be bound so that target molecules combine with the probe molecules. Alternatively still, antibody molecules may be bound to the surfaces of dendrimer molecules as probe molecules so that the protein of target molecules is extracted by means of antigen-antibody reaction.

Alternatively still, it is possible to adopt the desired number and shape of flow channels 2 formed in substrate 1, without being restricted to those discussed in the foregoing embodiments.

As is evident from the above description, the following advantageous effects are achieved according to the present invention.

(1) By forming dendrimer molecules in a flow channel through which a biopolymer solution flows and binding molecules of a probe biopolymer or antibody to the tips of the dendrimer molecules, it is possible to easily and efficiently retrieve molecules of a target biopolymer or protein by means of a complementary combination or antigen-antibody reaction.

(2) While the conventional method using magnetic beads requires mechanical moving parts, the present invention eliminates the need for such mechanical moving parts, making it possible to easily miniaturize the preprocessing area where a target biopolymer or protein is retrieved.

What is claimed is:

1. A method of dendrimer-based DNA extraction, comprising the steps of:

forming multibranched polyamide amine dendrimer molecules on walls of a U-shaped flow channel through which a solution containing target DNA is flowed;

binding probe DNA to tips of said multibranched polyamide amine dendrimer molecules; and extracting said target DNA by means of hybridization with said probe DNA.

2. The method of claim 1, wherein said dendrimer molecules are produced by providing aminosilane treatment on the walls of said U-shaped flow channel and overlaying a film of amidoamine, which is produced by the reaction of methyl acrylate with ethylenediamine, upon the aminosilane-treated area as a dendron unit.

* * * * *